(12) United States Patent
Sakuma et al.

(10) Patent No.: US 9,476,863 B2
(45) Date of Patent: Oct. 25, 2016

(54) GAS SENSOR WITH POROUS PROTECTION LAYERS

(71) Applicant: NGK SPARK PLUG CO., LTD., Nagoya-shi, Aichi (JP)

(72) Inventors: Shun Sakuma, Inuyama (JP); Masaki Onkawa, Konan (JP); Toru Iwano, Komaki (JP); Tatsuhiko Muraoka, Komaki (JP); Shigehiro Ohtsuka, Gifu (JP); Masaki Mizutani, Niwa-gun (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 155 days.

(21) Appl. No.: 14/485,438

(22) Filed: Sep. 12, 2014

(65) Prior Publication Data
US 2015/0075254 A1 Mar. 19, 2015

(30) Foreign Application Priority Data
Sep. 17, 2013 (JP) ................................. 2013-191960

(51) Int. Cl.
*G01N 27/407* (2006.01)
*G01N 33/00* (2006.01)
*G01M 15/10* (2006.01)

(52) U.S. Cl.
CPC ........ *G01N 33/0036* (2013.01); *G01M 15/104* (2013.01); *G01N 27/4072* (2013.01); *G01N 27/4077* (2013.01); *G01N 33/006* (2013.01)

(58) Field of Classification Search
CPC ..................... G01N 27/4071; G01N 27/4072; G01N 27/4077; G01N 27/4118; G01N 27/4075; G01N 27/4078; F01N 2560/02; F01N 2560/025; F01N 2560/026; F01N 2560/027
USPC .................................................. 204/428, 429
See application file for complete search history.

(56) References Cited

U.S. PATENT DOCUMENTS

2012/0211362 A1* 8/2012 Onkawa ............. G01N 27/4077
204/424

FOREIGN PATENT DOCUMENTS

JP 2012-220293 A 11/2012

* cited by examiner

*Primary Examiner* — Justin Olamit
(74) *Attorney, Agent, or Firm* — Stites & Harbison, PLLC; Jeffrey A. Haeberlin; James R. Hayne

(57) ABSTRACT

A gas sensor element comprises an elongated plate-like element including, at a forward end portion, a detecting section comprising a solid electrolyte body having an outer surface and a back surface, a detection electrode on the outer surface and a reference electrode on the back surface, and a porous layer covering the detection electrode. The coating layer includes a first protection layer entirely covering the detecting section, and a second protection layer circumferentially covering the first protection layer and extending at least from a forward end of the first protection layer to a position located rearward of the porous layer. The thickness of the first protection layer on the porous layer is larger than that of the first protection layer rearward of the porous layer. The thickness of the second protection layer rearward of the porous layer is larger than that of the second protection layer above the porous layer.

8 Claims, 12 Drawing Sheets

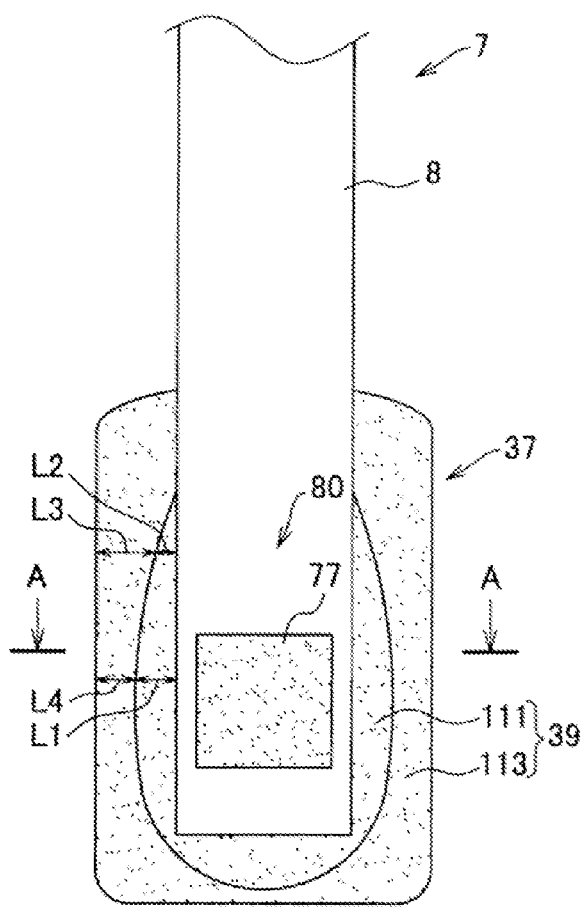
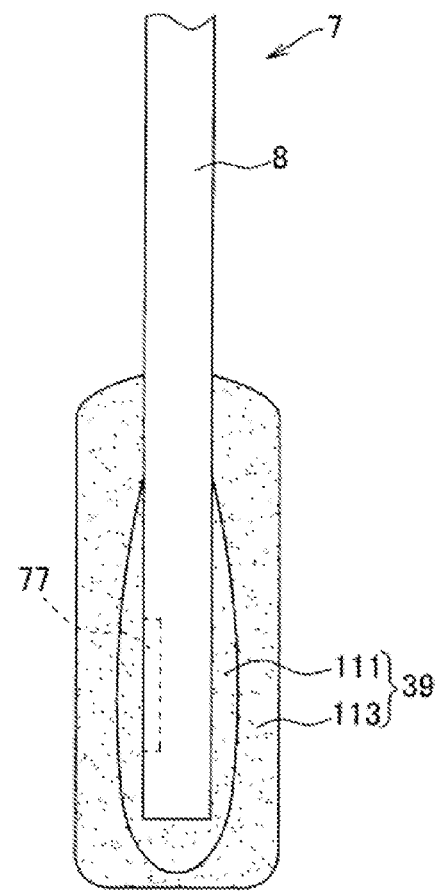
FIG. 4A  FIG. 4B
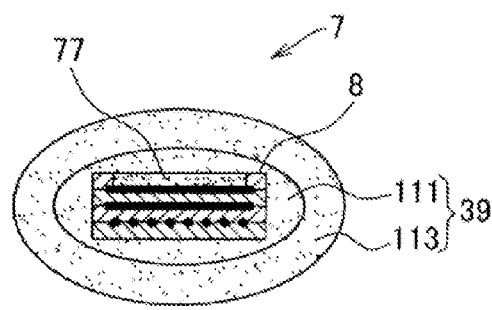
FIG. 4C

GAS SENSOR WITH POROUS PROTECTION LAYERS

CROSS REFERENCE TO RELATED APPLICATIONS

The present application claims priority from Japanese Patent Application No. 2013-191960, which was filed on Sep. 17, 2013, the disclosure of which is herein incorporated by reference in its entirety.

BACKGROUND OF THE INVENTION

1. Field of the Invention

The present invention relates to a gas sensor element and a gas sensor for detecting the concentration of a particular gas contained in, for example, combustion gas or exhaust gas of a combustor or an internal combustion engine.

2. Description of Related Art

Conventionally, various gas sensors are used for detecting the concentration of a particular component (oxygen, etc.) in exhaust gas of an internal combustion engine.

Such a gas sensor has a gas sensor element incorporated therein. The gas sensor element includes a ceramic plate-like element which encompasses a detecting section having a solid electrolyte body and a pair of electrodes disposed on the solid electrolyte body.

One end portion (forward end portion) of the gas sensor element at which the detecting section of the plate-like element is located is exposed to exhaust gas. Accordingly, water, such as water droplets contained in exhaust gas and condensed water formed in an exhaust pipe, and poisoning substances, such as silicon and phosphorus, contained in exhaust gas may adhere to the plate-like element. Particularly, adhesion of water to the plate-like element may cause the occurrence of damage, such as cracking, to the plate-like element.

Thus, in order to capture poisoning substances and to prevent direct contact of water with the plate-like element, a forward end portion of the gas sensor element is covered with a porous protection layer formed of ceramic (refer to Patent Document 1).

Also, as shown in FIG. 12, the following technique has been developed: a porous protection layer P3 which covers a detecting section P2 located at a forward end portion of a gas sensor element P1 has a two-layer structure composed of a lower layer P4 and an upper layer P5 (which covers the entire surface of the lower layer P4).

One of methods of forming the porous protection layer P3 having the two-layer structure utilizes the dipping process described in Patent Document 1; specifically, a forward end portion of the gas sensor element P1 is dipped in a material slurry a plurality of times to form the lower layer P4 and the upper layer P5.

RELATED ART DOCUMENTS

Patent Document 1 is Japanese Patent Application Laid-Open (kokai) No. 2012-220293.

BRIEF SUMMARY OF THE INVENTION

However, the above-mentioned conventional technique can form the porous protection layer P3 having two-layer structure, but may fail to provide sufficient resistance to adhesion of water, due to small thickness of a rear end portion (in FIG. 12, an upper portion) of the porous protection layer P3.

Specifically, in order for the upper layer P5 to cover the entire lower layer P4, the upper layer P5 is wider than the lower layer P4 in range of formation. Accordingly, a rear end portion of the porous protection layer P3 is composed of only a single layer; i.e., only the upper layer P5. Furthermore, since the material slurry is apt to move downward; i.e., forward, because of gravity, the thickness of a rear portion of the upper layer P5 becomes small.

Thus, when water adheres, from outside, to a rear end portion (a portion composed of only the upper layer P5) of the porous protection layer P3, water penetrates into the upper layer P5 (having small thickness) and comes into contact with the ceramic plate-like element P6; as a result, the plate-like element P6 is apt to crack.

The present invention has been conceived in view of the above problem, and an object of the present invention is to provide a gas sensor element having high resistance to adhesion of water, as well as a gas sensor which uses the gas sensor.

(1) According to a first aspect of the present invention, a gas sensor element comprises an elongated plate-like element and a coating layer. The plate-like element includes a detecting section at its forward end portion. The detecting section comprises a solid electrolyte body having an outer surface and a back surface, a detection electrode on the outer surface (i.e., located externally of the plate-like element) and a reference electrode on the back surface, and a porous layer covering the detection electrode. The coating layer includes a first protection layer and a second protection layer. The first protection layer entirely covers the detecting section. The second protection layer circumferentially covers the first protection layer and extends at least from a forward end of the first protection layer to a position located rearward of the porous layer. In the gas sensor element, the thickness of the first protection layer on the porous layer is larger than that of the first protection layer rearward of the porous layer. Furthermore, the thickness of the second protection layer rearward of the porous layer is larger than that of the second protection layer above the porous layer.

According to the first aspect, the thickness of the first protection layer on the porous layer is larger than that of the first protection layer at a position located rearward of the porous layer. Furthermore, the thickness of the second protection layer at a position located rearward of the porous layer is larger than that of the second protection layer above the porous layer.

That is, the first protection layer is thinner at a portion located rearward of the porous layer than at a portion located on the porous layer. By contrast, the second protection layer is thicker at a portion located rearward of the porous layer than at a portion located above the porous layer. Accordingly, as compared with a conventional coating layer, the coating layer of the present invention can have a larger thickness at its rear portion. As a result, even in the event of adhesion of water to a rear portion of the coating layer, the plate-like element (accordingly, the gas sensor element) is unlikely to suffer, for example, cracking, whereby resistance to adhesion of water is improved.

The thickness of each of the protection layers on or above the porous layer can be represented by, for example, a thickness at a typical position (e.g., a thickness at a longitudinally mid position) on or above the porous layer, or an average thickness along the longitudinal direction on or above the porous layer. The thickness of each of the protection layers at a position located rearward of the porous layer can be represented by, for example, a thickness at a typical position (e.g., a thickness at a longitudinally mid position between the rear end of the porous layer and the rear end of each of the protection layers) or an average thickness along the longitudinal direction of that portion of each of the protection layers which extends rearward from the porous layer.

(2) A second mode of the present invention is characterized in that, in a region where the first protection layer and the second protection layer of the coating layer are superposed on each other along a longitudinal direction of the plate-like element, the difference between a largest thickness and a smallest thickness of the coating layer is 100 μm or less.

According to the second mode, the difference between the largest thickness and the smallest thickness of the coating layer is 100 μm or less, indicating that the coating layer has a substantially uniform thickness along the longitudinal direction of the plate-like element.

Thus, in contrast to a conventional coating layer, a rear portion of the coating layer is not thin, thereby providing high resistance to adhesion of water.

(3) A third mode of the present invention is characterized in that the entire surface of the first protection layer is covered with the second protection layer (i.e., the second protection layer entirely covers the first protection layer), and a rear end portion of the coating layer has a single-layer structure comprising the second protection layer.

As compared with a conventional coating layer, the coating layer of the third mode is larger in thickness at a rear single-layer portion (second protection layer) of the coating layer, thereby providing high resistance to adhesion of water.

(4) A fourth mode of the present invention is characterized in that a forward portion of the first protection layer is covered with the second protection layer (i.e., the second protection layer covers a forward portion of the first protection layer), and a rear end portion of the coating layer has a single-layer structure comprising the first protection layer.

As compared with a conventional coating layer, the coating layer of the fourth mode is larger in thickness at a rear single-layer portion (first protection layer) of the coating layer, thereby providing high resistance to adhesion of water.

(5) A fifth mode of the present invention is characterized in that the first protection layer is higher in percentage of pores than the second protection layer.

According to the fifth mode, the inner first protection layer has a large number of large pores, whereas the outer second protection layer has a small number of large pores. Thus, even when water adheres to the surface (outer surface) of the outer second protection layer and penetrates into the second protection layer, water is likely to stagnate, by capillarity, within the outer second protection layer having a small number of large pores and is thus unlikely to penetrate into the inner first protection layer having a large number of large pores. Therefore, high resistance to adhesion of water is provided.

The percentage of pores can be represented by, for example, porosity.

(6) A sixth mode of the present invention is characterized in that the second protection layer is thicker than the first protection layer in the entire region of the coating layer.

According to the sixth mode, the coating layer has such a structure that the second protection layer is thicker than the first protection layer in the entire region of the coating layer. Therefore, sufficient resistance to adhesion of water is ensured.

(7) A seventh mode of the present invention is characterized by further comprising a heater disposed in the plate-like element in a region which is superposed on the detecting section as viewed from a thickness direction of the plate-like element.

According to the seventh mode, the heater is formed at a position corresponding to the detecting section, whereby the heater can efficiently heat the detecting section.

(8) In accordance with another aspect of the present invention, a gas sensor includes a gas sensor element, as described above, for detecting the concentration of a particular gas component in gas to be measured, and a housing for holding the gas sensor element.

Since the gas sensor includes the above-described gas sensor element, the gas sensor exhibits high resistance to adhesion of water.

BRIEF DESCRIPTION OF THE DRAWINGS

Illustrative aspects of the invention will be described in detail with reference to the following figures wherein:

FIG. 4A is a front view showing a forward end portion of the gas sensor element of the first embodiment by removing a coating layer from a front surface of the forward end portion.

FIG. 4B is a side view showing the forward end portion of the gas sensor element by removing the coating layer from a side surface of the forward end portion.

FIG. 4C is a sectional view taken along line A-A of FIG. 4A.

DETAILED DESCRIPTION OF EXEMPLARY EMBODIMENTS OF THE INVENTION

Embodiments of a gas sensor element and a gas sensor of the present invention will next be described with reference to the drawings.

A. First Embodiment:

a) First, the configuration of a gas sensor having a gas sensor element of the present embodiment will be described.

Figure 1:
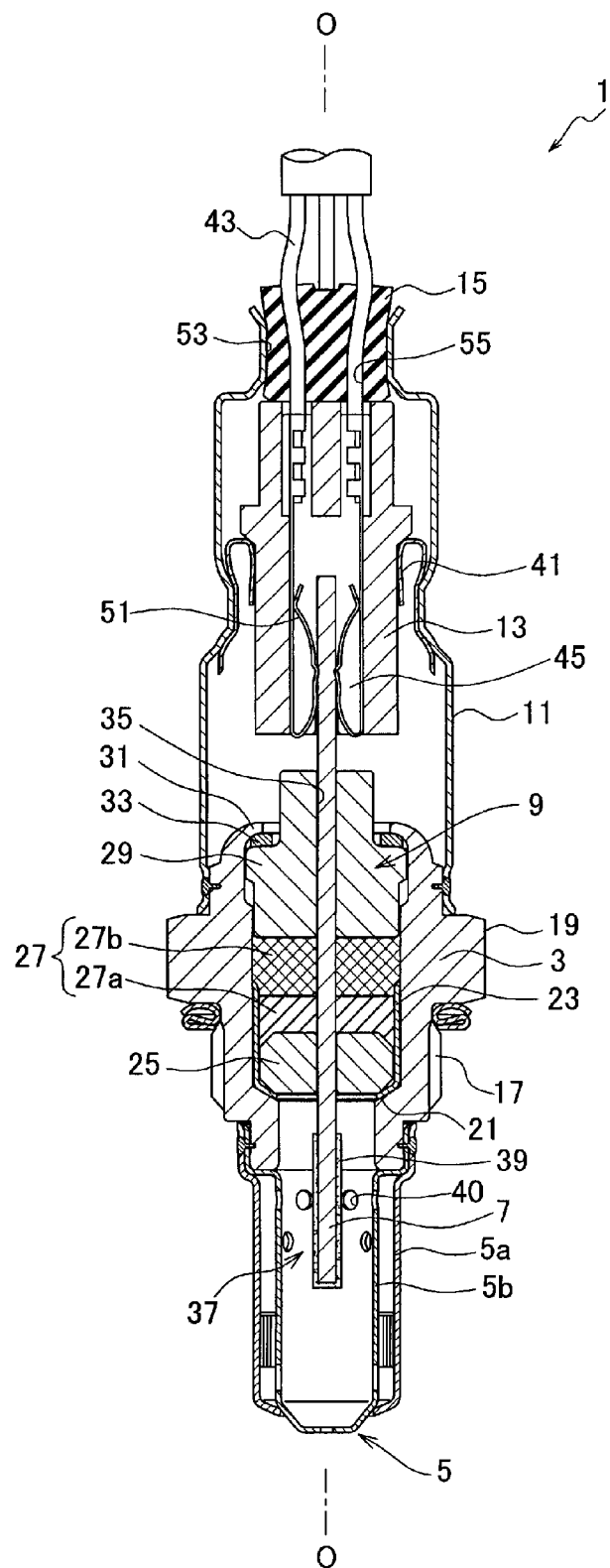
FIG. 1 is an explanatory view showing, in an axially cutaway condition, a gas sensor of a first embodiment of the present invention.

As shown in FIG. 1, a gas sensor 1 of the present embodiment is an oxygen sensor mounted to an exhaust pipe of an internal combustion engine and used to measure oxygen concentration in exhaust gas.

The gas sensor 1 includes a metallic shell 3; a protector 5 disposed on the forward side (lower side in FIG. 1) of the metallic shell 3; a gas sensor element 7 held in the interior (on the inner-circumference side) of the metallic shell 3; a holding structure 9 disposed within the metallic shell 3 and adapted to hold the gas sensor element 7; a tubular housing 11 disposed on the rear side of the metallic shell 3; a separator 13 disposed within the tubular housing 11; and a rubber cap 15 plugged into a rear end portion of the tubular housing 11. The configurational features of the gas sensor 1 will be described below.

The metallic shell 3 is a tubular member formed of a heat resisting metal and externally has an externally threaded portion 17 for mounting the gas sensor 1 to an exhaust pipe, and a hexagonal portion 19 with which a mounting tool is engaged for mounting work. The metallic shell 3 also has a metallic-shell-side stepped portion 21 protruding radially inward.

The holding structure 9 includes, from the forward side, a metal holder 23 supported by the metallic-shell-side stepped portion 21 and adapted to hold the gas sensor element 7; a ceramic holder 25 disposed within the metal holder 23 for disposing the gas sensor element 7 at a predetermined position; talc 27; and a ceramic sleeve 29 placed on the talc 27.

The talc 27 is composed of first talc 27a and second talc 27b. The first talc 27a is compressed in a filling manner within the metal holder 23 to ensure airtightness between the inner surface of the metal holder 23 and the outer surface of the gas sensor element 7. The second talc 27b is compressed in a filling manner on the first talc 27a to ensure airtightness between the inner surface of the metallic shell 3 and the outer surface of the gas sensor element 7.

Also, the metallic shell 3 has a crimped portion 31 provided at a rear end portion in an inwardly bent manner to press the ceramic sleeve 29 toward the forward end of the metallic shell 3 through a ring member 33 of stainless steel.

The ceramic sleeve 29 and the ceramic holder 25 have an axial hole 35 extending therethrough along an axial line O for allowing the gas sensor element 7 to be inserted therethrough (thus, through the holding structure 9).

As will be described in detail later, the gas sensor element 7 is an elongated plate-like member (having rectangular main surfaces and side surfaces) extending vertically in FIG. 1. The gas sensor element 7 is held axially at the center of the metallic shell 3 by the holding structure 9 in such a manner that its forward and rearward end portions protrude from the metallic shell 3.

The gas sensor element 7 has a coating layer 39 formed thereon in such a manner as to cover its forward end portion 37; i.e., to cover its portion protruding from the holding structure 9 (more specifically, to cover its portion protruding forward from the metal holder 23).

The forward end portion 37 of the gas sensor element 7 is mostly covered with the coating layer 39; however, the rear end of the coating layer 39 is not in contact with the metal holder 23, leaving a clearance therebetween. On a front view (on a view from a direction perpendicular to paper on which FIG. 1 appears) of the gas sensor 1, the coating layer 39 extends up to a position located rearward (in FIG. 1, upward) of the forward end of the metallic shell 3.

The protector 5 is a tubular member of metal having a plurality of gas intake holes 40, covers the forward end portion 37 of the gas sensor element 7 protruding from the forward end of the metallic shell 3, and is externally welded to a forward end portion of the metallic shell 3.

The protector 5 has the following dual structure: a closed-bottomed cylindrical inner protector 5b is disposed in a closed-bottomed cylindrical outer protector 5a in such a manner that a forward end portion of the inner protector 5b protrudes from the forward end of the outer protector 5a.

The tubular housing 11 is a metal member whose forward end portion is externally fitted and laser-welded to a rear end portion of the metallic shell 3 and which accommodates the separator 13 in its rear end portion.

The separator 13 is an electrically insulating tubular member formed of ceramic and is held by a holding member 41 having an elastic form and disposed between the separator 13 and the tubular housing 11.

The separator 13 has an insertion hole 45 formed therethrough for allowing a plurality of (four) lead wires 43 (FIG. 1 shows only three lead wires 43) inserted through the insertion hole 45 and electrically connected to the gas sensor element 7. The insertion hole 45 also accommodates therein a plurality of (four) connection terminals 51 (FIG. 1 shows only part of them) adapted to electrically connect the lead wires 43 to respective leads 47 and 49 (see FIG. 2).

The rubber cap 15 is a substantially circular columnar member for plugging up a rear end opening portion 53 of the tubular housing 11. The rubber cap 15 has a plurality of (four) insertion holes 55 through which the respective lead wires 43 are inserted.

b) Next, the gas sensor element 7 will be described.

Figure 2:
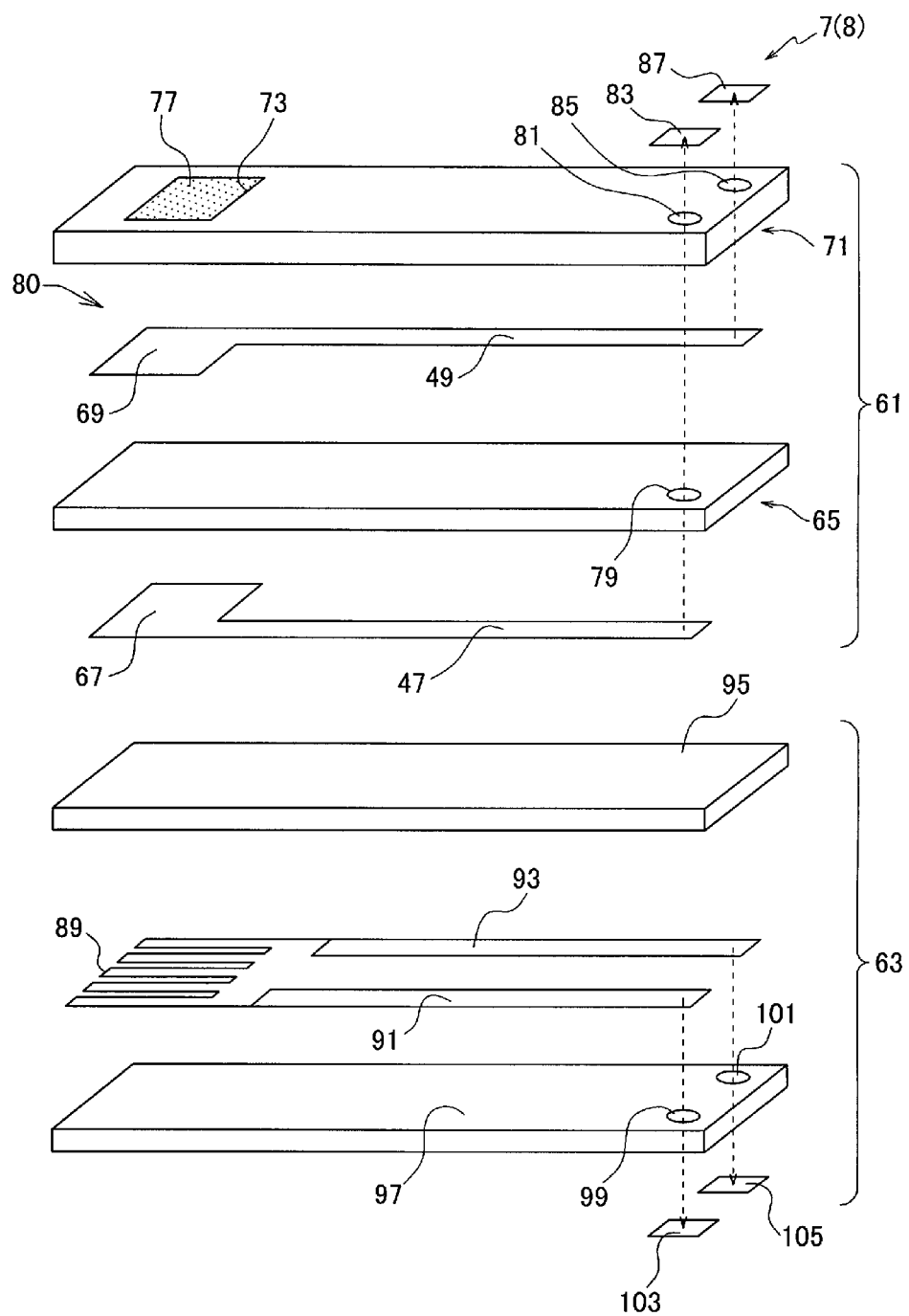
FIG. 2 is an exploded perspective view showing a gas sensor element of the first embodiment.

As shown in FIG. 2 in an exploded manner, the gas sensor element 7 is an elongated rectangular-parallelepiped plate-like member and is a laminate of a plate-like detection element 61 and a plate-like heater element 63. In FIG. 2, the coating layer 39 is omitted. Hereinafter, the gas sensor element 7 having no coating layer 39 is called a gas sensor element body 8. The configurational features of the gas sensor element 7 will be described below.

The detection element 61 includes a solid electrolyte layer 65 formed of, for example, a zirconia ($ZrO_2$)-based sintered body or an $LaGaO_3$-based sintered body which contains yttria ($Y_2O_3$) or calcia (CaO) as stabilizer.

The solid electrolyte layer 65 has a reference electrode 67 formed, at its forward end portion (its left end portion in FIG. 2), on a surface located toward the heater element 63 and has a detection electrode (outer electrode) 69 formed on a surface (an outer surface, or an upper surface in FIG. 2) opposite the reference electrode 67. The leads 47 and 49 extend from the reference electrode 67 and the detection electrode 69, respectively, along the longitudinal direction of the solid electrolyte layer 65. The electrodes 67 and 69 and the leads 47 and 49 are formed of an electrically conductive substance, such as Pt.

A dense first ceramic layer 71 is disposed on the outside of the solid electrolyte layer 65 in such a manner as to cover the detection electrode 69 and the lead 49. Furthermore, the first ceramic layer 71 has an opening 73 at a position corresponding to the detection electrode 69 and has, in the opening 73, a porous electrode protection layer (a porous layer) 77 for protecting the detection electrode 69 from poisoning. Examples of material used to form the first ceramic layer 71 include alumina, spinel, mullite, and zirconia. An example material for the porous layer 77 is alumina.

A detecting section 80 is composed of the reference electrode 67 and the lead 47, the detection electrode 69 and the lead 49, the solid electrolyte layer 65 sandwiched between the electrodes and the leads, and the porous layer 77 which covers the detection electrode 69.

An end of the lead 47 is connected to a signal output terminal 83 through a through hole 79 extending through the solid electrolyte layer 65 and a through hole 81 extending through the first ceramic layer 71, whereas the signal output terminal 83 is connected to a corresponding external terminal. An end of the lead 49 is connected to a signal output terminal 87 through a through hole 85 extending through the first ceramic layer 71, whereas the signal output terminal 87 is connected to a corresponding external terminal.

The heater element 63 includes a resistance heat-generating element 89, a pair of leads 91 and 93 extending from the resistance heat-generating element 89, and a second ceramic layer 95 and a third ceramic layer 97 which hold the resistance heat-generating element 89 and the leads 91 and 93 therebetween.

The resistance heat-generating element 89 and the detecting section 80 are superposed on each other (as viewed from the plate thickness direction (the vertical direction in FIG. 2)).

Examples of materials used to form the resistance heat-generating element 89 and the leads 91 and 93 include noble metals, tungsten, and molybdenum. Examples of noble metals include Pt, Au, Ag, Pd, Ir, Ru, and Rh. Examples of material used to form the second ceramic layer 95 and the third ceramic layer 97 include electrically insulating alumina and mullite.

Ends of the leads 91 and 93 are connected to heater terminals 103 and 105, respectively, through respective through holes 99 and 101 extending through the third ceramic layer 97.

c) Next, the constitution of an essential portion of the present embodiment; specifically, the constitution of the forward end portion 37 of the gas sensor element 7, will be described.

Figure 3:
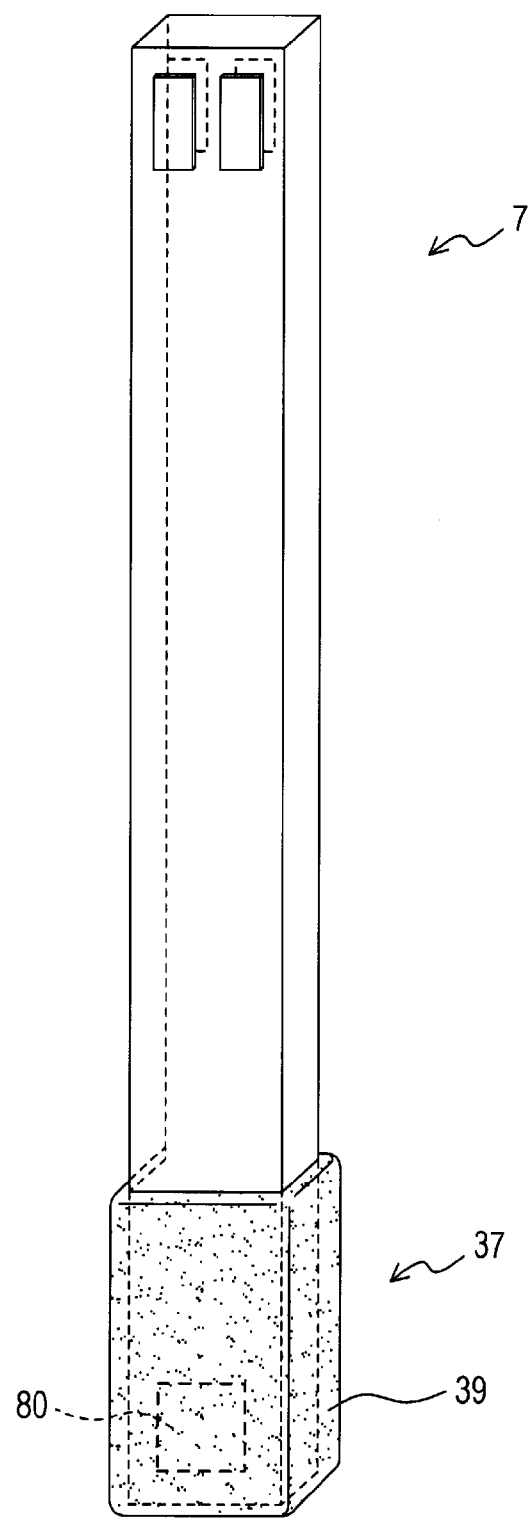
FIG. 3 is a perspective view showing the gas sensor element of the first embodiment.

As shown in FIG. 3, the forward end portion 37 of the gas sensor element 7 has the porous coating layer 39 formed in such a manner as to cover the forward end portion (more specifically, the detecting section 80).

As shown in FIG. 4, the coating layer 39 has an external shape resembling a rectangular parallelepiped. The coating layer 39 is composed of a lower layer (first protection layer) 111 which is in close contact with an outer surface of the gas sensor element 7, and an upper layer (second protection layer) 113 which covers the entire surface of the first protection layer 111 and extends rearward (upward in FIG. 4A) from the first protection layer 111 to be in close contact with an outer surface of the gas sensor element 7.

The first protection layer 111 is a porous layer formed of, for example, particles of ceramic selected singly or in combination from the group consisting of titania, spinel, alumina, zirconia, zircon, and cordierite and having a porosity of, for example, 35% to 70% and an average pore diameter of 10 μm to 30 μm. The second protection layer 113 is a porous layer formed of, for example, particles of ceramic selected singly or in combination from the group consisting of titania, spinel, alumina, zirconia, zircon, and cordierite and having a porosity of, for example, 10% to 50% and an average pore diameter of 0.05 μm to 10 μm.

Notably, the first protection layer 111 is higher in porosity and larger in average pore diameter than the second protection layer 113. That is, the first protection layer 111 is higher in percentage of pores than the second protection layer 113. More specifically, the inner first protection layer 111 has a large number of large-diameter pores, whereas the outer second protection layer 113 has a small number of large-diameter pores.

The first protection layer 111 has an external shape resembling an axially elongated (vertically elongated in FIG. 4A) sphere (spindle shape) and thus has an elliptical cross section. That is, the distribution of radial thicknesses (thicknesses in a direction perpendicular to the axial direction) of the first protection layer 111 follows a convex shape such that the thickness assumes a largest value (peak value) in a region corresponding to the porous layer 77 (on the porous layer 77) and reduces (becomes thinner) forward and rearward from the peak.

Specifically, the radial thickness of the first protection layer 111 is the largest at an axially central portion corresponding to the porous layer 77 and reduces from the central portion along the vertical direction of FIG. 4A (the thickness of a lower end portion is excluded, and the same also applies in the following description). Therefore, the first protection layer 111 reduces, in thickness, rearward (upward in FIG. 4A) from the central portion.

The second protection layer 113 has an external shape resembling a rectangular parallelepiped. The thickness of the second protection layer 113 is small at a portion corresponding to a large-thickness portion (a central portion at which a peak thickness exists) of the first protection layer 111 and is large at portions corresponding to small-thickness portions (a rear portion and a forward portion) of the first protection layer 111. A rear end portion of the coating layer 39 has a single-layer structure composed of the second protection layer 113.

Specifically, as shown in FIG. 4A, in the present embodiment, the thickness (L1) of the first protection layer 111 on the porous layer 77 (e.g., at the position of the aforementioned peak) of the gas sensor element 7 is larger than the thickness (L2) of the first protection layer 111 at a position located rearward of the porous layer 77 (e.g., at a position located 2 mm rearward from the rear end of the porous layer 77). Furthermore, the thickness (L3) of the second protection layer 113 at a position located rearward of the porous layer 77 (e.g., at the position located 2 mm rearward from the rear end of the porous layer 77) is larger than the thickness (L4) of the second protection layer 113 above the porous layer 77 (e.g., at the position of the peak).

Furthermore, in the present embodiment, in a region where the first protection layer 111 and the second protection layer 113 are superposed on each other as viewed from the plate thickness direction (the horizontal direction in FIG. 4B) of the gas sensor element 7 and from a direction (the horizontal direction in FIG. 4A) perpendicular to the plate thickness direction, the difference between the largest thickness and the smallest thickness of the coating layer 39 is 100 µm or less, indicating that the thickness of the coating layer 39 is substantially uniform.

That is, at a portion of the coating layer 39 where the first protection layer 111 is thick, the second protection layer 113 is thin; by contrast, at a portion of the coating layer 39 where the first protection layer 111 is thin (or does not exist), the second protection layer 113 is thick. Accordingly, the thickness of the coating layer 39 is substantially uniform along the axial direction. A portion of the coating layer 39 where the first protection layer 111 does not exist; i.e., that portion of the coating layer 39 which is located rearward of the first protection layer 111 has a single-layer structure composed of only the second protection layer 113.

Furthermore, the thickness of the second protection layer 113 is larger than that of the first protection layer 111 along the entire circumference of the coating layer 39.

Also, a smallest thickness of the second protection layer 113 at a position (on the first protection layer 111) located rearward of the porous layer 77 is larger than a largest thickness of the second protection layer 113 above the porous layer 77. Meanwhile, a smallest thickness of the first protection layer 111 on the porous layer 77 is larger than a largest thickness of the first protection layer 111 at a position located rearward of the porous layer 77.

The gas sensor element 7 including the coating layer 39 has preferably a longitudinal length of 70 mm to 105 mm, a width of 2.5 mm to 6 mm, and a thickness of 1 mm to 3 mm and has, in the present embodiment, a longitudinal length of about 85 mm, a width of about 3 mm, and a thickness of about 2 mm.

d) Next, a method of manufacturing the gas sensor element 7 will be described.

Method of Manufacturing Gas Sensor Element Body 8

First, a method of manufacturing the gas sensor element body 8, which is a base member of the gas sensor element 7, will be described.

First, 20% by mass alumina powder was added to yttria-stabilized zirconia powder; the resultant mixture and binder (polyvinyl butyral) were mixed to form paste; and the paste was used to form a green solid electrolyte sheet which was to become the solid electrolyte layer 65. The green solid electrolyte sheet has such a size as to be able to form a plurality of elements by cutting.

Subsequently, through holes which were to become the through holes 79 were formed in the green solid electrolyte sheet at predetermined positions.

Next, electrically conductive paste which predominantly contained platinum was applied, by printing in predetermined patterns, onto the green solid electrolyte sheet in predetermined regions, followed by drying, thereby forming electrically conductive patterns which were to become the detection electrodes 69, the reference electrodes 67, and the leads 47 and 49. Also, the electrically conductive paste was applied to the wall surfaces of the through holes which were to become the through holes 79. Thus, a green element sheet was yielded.

Next, by use of paste formed by mixing alumina powder and binder (polyvinyl butyral), green alumina sheets which were to become the first, second, and third ceramic layers 71, 95, and 97 were prepared. Through holes which were to become the openings 73 were formed in the green alumina sheet which was to become the first ceramic layers 71. Through holes which were to become the through holes 99 and 101 were formed in the green alumina sheet which was to become the third ceramic layers 97.

Subsequently, electrically conductive paste similar to that mentioned above was applied, by printing in predetermined patterns, onto the front and back surfaces, in predetermined regions, of the green alumina sheet which was to become the third ceramic layers 97, followed by drying, thereby forming electrically conductive patterns which were to become the resistance heat-generating elements 89 and pairs of the heater terminals 103 and 105. Also, the electrically conductive paste was applied to the wall surfaces of the through holes which were to become the through holes 99 and 101.

Then, the green alumina sheet which was to become the second ceramic layers 95 was laminated compressively under reduced pressure onto the green alumina sheet which was to become the third ceramic layers 97, in such a manner that the electrically conductive patterns which were to become the resistance heat-generating elements 89 were sandwiched therebetween. Thus, a green heater sheet which was to become the heater elements 63 was yielded.

Next, the green element sheet and the green heater sheet were laminated together. Furthermore, the green alumina sheet which was to become the first ceramic layer 71 was laminated on the green element sheet.

Furthermore, slurry was prepared by mixing alumina powder, carbon powder as a pore-forming material, polyvinyl butyral as binder, and a dispersant. The slurry was charged in a filling manner into the through holes which were to become the openings 73, whereby the charged slurry which was to become the porous layers 77 was laminated on the electrically conductive patterns which were to become the detection electrodes 69. The resultant laminate was compressed under reduced pressure, thereby yielding an assembly.

Then, the assembly was cut into 10 green laminates by a publicly known method. The green laminates were debindered in the atmosphere and then fired at a temperature of 1,500° C. for one hour, thereby yielding the gas sensor element bodies 8 (elements before the coating layers 39 were formed).

Method of Forming Coating Layer 39

Next will be described a method of forming the coating layer 39 on a forward end portion of the gas sensor element body 8 through combination of a dipping process and a spraying process.

First will be described a method of preparing slurry (inner coating liquid) used in forming the first protection layer 111 by a dipping process.

A total of 60 vol. % to 80 vol. % of titania powder (average particle size <1 µm) and alumina fiber (average fiber length: 50 µm), 20 vol. % to 40 vol. % carbon powder (average particle size: 20 µm), and 10 wt. % alumina sol (outer formulation) were measured out and mixed. To the mixture was added organic solvent (e.g., ethanol, propylene glycol, or butyl carbitol), followed by stirring to yield slurry having appropriate viscosity.

The average particle size of the powder used to form the slurry was obtained by a laser diffraction method. The ceramic fiber length was obtained by averaging lengths of ceramic fibers before the ceramic fibers were mixed into the slurry.

Next, will be described a method of preparing slurry (outer coating liquid) used in forming the second protection layer 113 by a spraying process.

60 vol. % to 80 vol. % spinel powder (average particle size <40 µm to 50 µm), 20 vol. % to 40 vol. % titania powder (average particle size <1 µm), and 10 wt. % alumina sol (outer formulation) were measured out and mixed. To the mixture was added organic solvent (e.g., ethanol, propylene glycol, or butyl carbitol), followed by stirring to yield slurry having appropriate viscosity.

The average particle size of the powder used to form the slurry was obtained by a laser diffraction method.

By use of the above-mentioned two types of slurries, the coating layer 39 was formed by the following method.

Specifically, first, a forward end portion of the gas sensor element body 8 was immersed in the inner coating liquid to form an inner coating layer (not shown) having a predetermined thickness (e.g., a largest thickness of 200 μm) on the forward end portion of the gas sensor element body 8.

Next, in order to volatilize excess organic solvent in the inner coating liquid, the gas sensor element body 8 having the inner coating layer formed thereon was displaced in a drier having a temperature of 20° C. to 200° C. and was dried for several hours.

Next, the outer coating liquid was sprayed on the dried inner coating layer to form an outer coating layer (not shown) having a predetermined thickness (e.g., a largest thickness of 400 μm) on the inner coating layer.

Figure 5A:
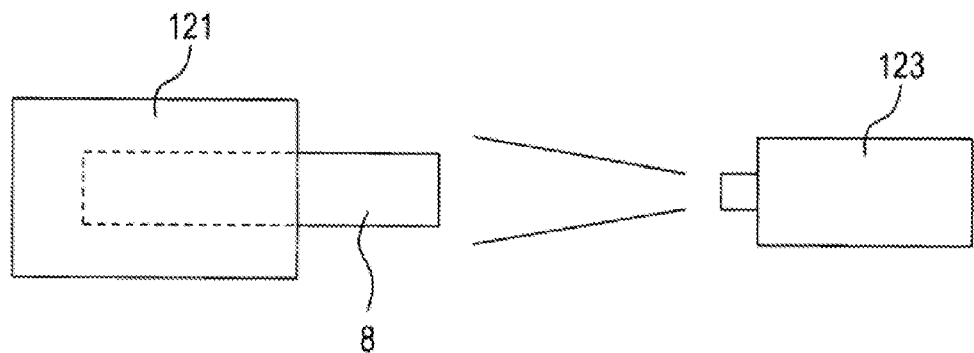
FIG. 5A is an explanatory view showing a step in a method of forming the coating layer of the gas sensor element of the first embodiment.

Specifically, as shown in FIG. 5A, in a condition in which the gas sensor element body 8 was supported at a rear end portion by a support member 121, the outer coating liquid was sprayed from a forward direction by use of a spraying device 123 having a needle nozzle so as to apply the outer coating liquid onto the inner coating layer formed on a forward end portion of the gas sensor element body 8.

Figure 5B:
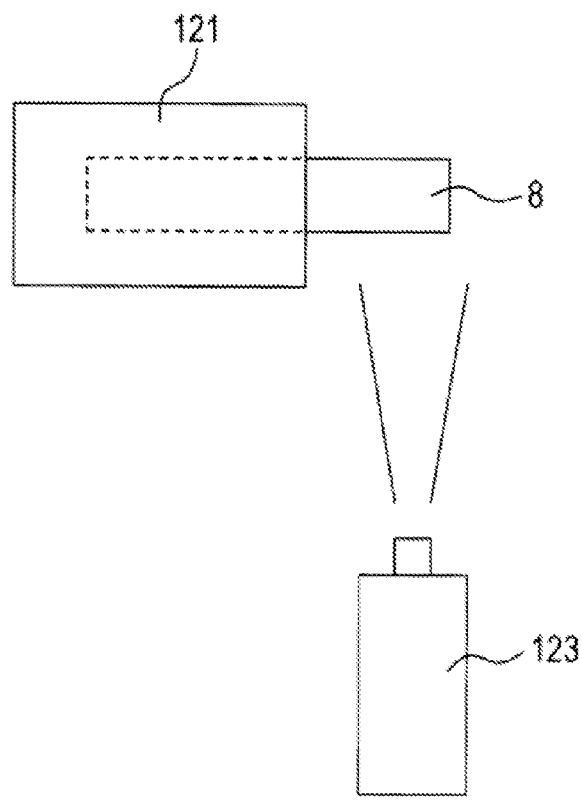
FIG. 5B is an explanatory view showing another step in the method of forming the coating layer.

Next, as shown in FIG. 5B, while the gas sensor element body 8 was being rotated, the outer coating liquid was sprayed from a side direction by use of the spraying device 123 so as to apply the outer coating liquid onto not only the surface of the inner coating layer but also a portion of the gas sensor element body 8 located rearward of the inner coating layer (e.g., a portion extending about 3 mm rearward from the rear end of the inner coating layer).

The position (rear end position) of the outer coating layer formed by use of the outer coating liquid can be freely adjusted by, for example, masking the surface of a portion of the gas sensor element body 8 on which the outer coating layer is not to be formed.

Particularly, according to the present embodiment, in the case of forming the outer coating layer by applying the outer coating liquid onto the inner coating layer, at a large-thickness portion of the inner coating layer, a large amount of the applied outer coating liquid is absorbed into pores of the inner coating layer; accordingly, as shown in FIGS. 4A and 4B, the thickness of the outer coating layer becomes small. By contrast, at a small-thickness portion of the inner coating layer (or in a region where the inner coating layer does not exist), the outer coating liquid is unlikely to be absorbed into pores of the inner coating layer (or the outer coating liquid is not absorbed into the inner coating layer); accordingly, the thickness of the outer coating layer becomes large. As a result, the coating layer (coating layer 39) composed of the inner coating layer and the outer coating layer has substantially uniform thickness as a whole.

Subsequently, the gas sensor element body 8 having the thus-formed inner and outer coating layers was fired at a temperature of 900° C. to 1,100° C. in the atmosphere for three hours, thereby completing the gas sensor element 7.

According to the present embodiment, after formation of the inner coating layer and the outer coating layer, the inner coating layer and the outer coating layer are fired simultaneously. However, the following process may be employed: after the inner coating layer is fired, the outer coating layer is fired.

The gas sensor element 7 manufactured by the above method is assembled to a housing and other members according to a usual method, whereby the gas sensor 1 can be manufactured.

e) Next, the effects of the present embodiment will be described.

In the present embodiment, the thickness of the first protection layer 111 on the porous layer 77 is larger than the thickness of the first protection layer 111 at a position located rearward of the porous layer 77. Furthermore, the thickness of the second protection layer 113 at a position located rearward of the porous layer 77 is larger than the thickness of the second protection layer 113 on the porous layer 77.

That is, the first protection layer 111 is smaller in thickness at a position located rearward of the porous layer 77 than on the porous layer 77; by contrast, the second protection layer 113 is larger in thickness at a position located rearward of the porous layer 77 than on the porous layer 77. Accordingly, as compared with a conventional coating layer, the coating layer 39 can have a larger thickness at its rear portion. As a result, even in the event of adhesion of water to a rear portion of the coating layer 39, the gas sensor element 7 is unlikely to suffer, for example, cracking, whereby resistance to adhesion of water is improved.

Furthermore, the coating layer 39 of the present embodiment is featured such that an adhering water droplet slowly penetrates thereinto while dispersing, thereby preventing a local occurrence of temperature gradient; therefore, the occurrence of cracking can be favorably prevented.

In the present embodiment, the difference between a largest thickness and a smallest thickness of the coating layer 39 is 100 μm or less, indicating that the coating layer 39 has substantially uniform thickness along the longitudinal direction of the gas sensor element 7. Thus, in contrast to a conventional coating layer, a rear portion of the coating layer 39 is not thin, thereby providing high resistance to adhesion of water.

In the present embodiment, the inner first protection layer 111 has a large number of pores (e.g., a large percentage of large pores), whereas the outer second protection layer 113 has a small number of pores. Thus, even when water adheres to the surface (outer surface) of the outer second protection layer 113 and penetrates into the second protection layer 113, by capillarity, water is unlikely to penetrate into the inner first protection layer 111 having a large number of pores. Therefore, high resistance to adhesion of water is provided.

In the present embodiment, the second protection layer 113 is thicker than the first protection layer 111 in the entire coating layer 39, whereby sufficient strength is ensured for the coating layer 39.

Second Embodiment

Next, a gas sensor element of a second embodiment will be described. Description of features similar to those of the first embodiment described above is omitted.

The present second embodiment differs from the first embodiment in the structure of the coating layer; therefore, the coating layer will be mainly described.

Figures 6A, 6B:
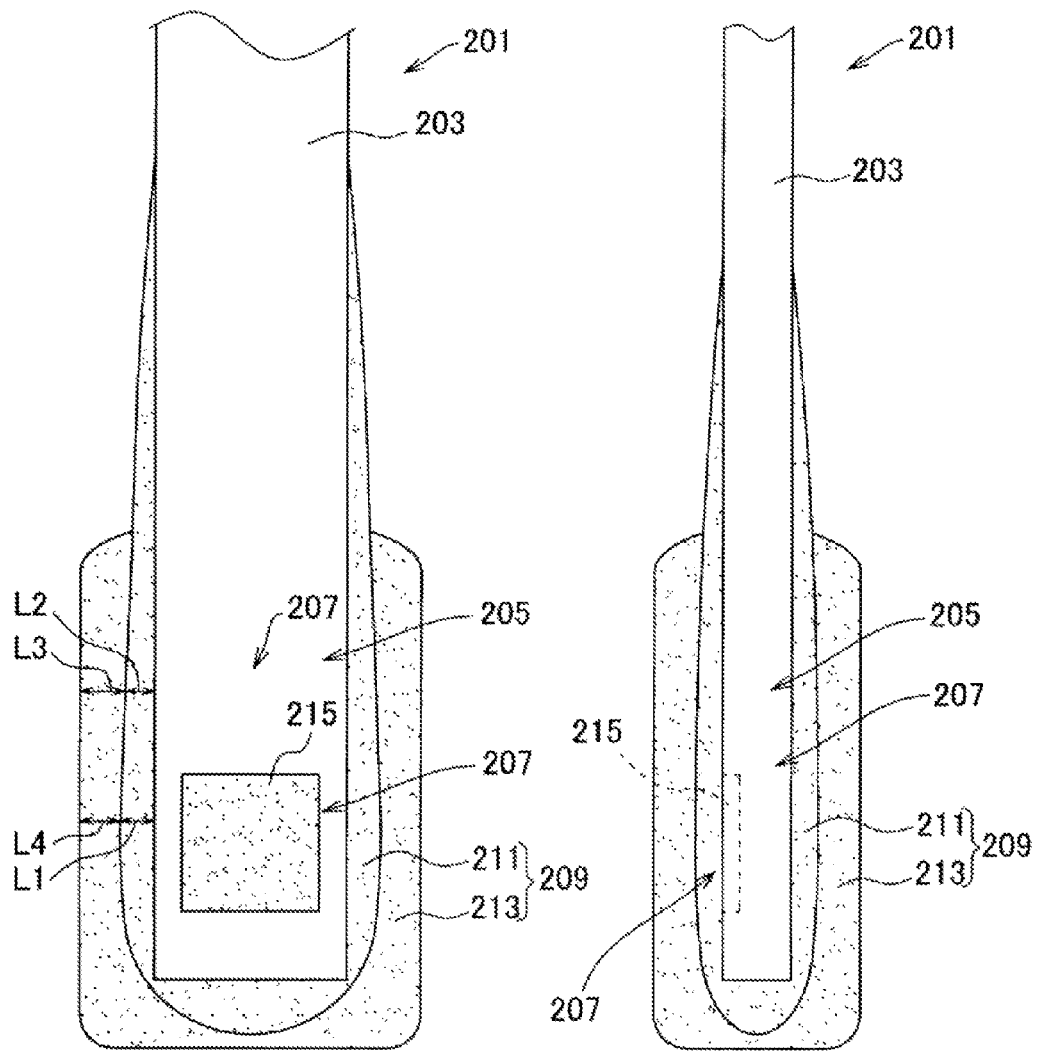
FIG. 6A is a front view showing a forward end portion of a gas sensor element of a second embodiment of the present invention by removing a coating layer from a front surface of the forward end portion.
FIG. 6B is a side view showing the forward end portion of the gas sensor element of the second embodiment by removing the coating layer from a side surface of the forward end portion.

As shown in FIG. 6, a gas sensor element 201 has a porous coating layer 209 formed thereon in such a manner as to cover a forward end portion 205 (thus, a detecting section 207) of a gas sensor element body 203 similar to that of the first embodiment.

The coating layer 209 is composed of a lower layer (first protection layer) 211 and an upper layer (second protection layer) 213. The first protection layer 211 and the second protection layer 213 are formed of material similar to that used in the first embodiment, but differ greatly from those of the first embodiment in shape and location.

More specifically, the first protection layer 211 extends rearward greatly than in the case of the first embodiment, and a rear portion of the second protection layer 213 is formed on the surface of the first protection layer 211 rather than on the surface of the gas sensor element body 203. Accordingly, a rear end portion of the coating layer 209 has a single-layer structure composed of the first protection layer 211.

In the second embodiment also, the thickness (L1) of the first protection layer 211 on a porous layer 215 of the gas sensor element 201 is larger than the thickness (L2) of the first protection layer 211 at a position located rearward of the porous layer 215. Furthermore, the thickness (L3) of the second protection layer 213 at a position located rearward of the porous layer 215 is larger than the thickness (L4) of the second protection layer 213 on the porous layer 215.

Furthermore, in a region where the first protection layer 211 and the second protection layer 213 of the coating layer 209 are superposed on each other as viewed from the plate thickness direction (the horizontal direction in FIG. 6B) of the gas sensor element 7 and from a direction (the horizontal direction in FIG. 6A) perpendicular to the plate thickness direction, the difference between the largest thickness and the smallest thickness of the coating layer 209 is 100 μm or less, indicating that the thickness of the coating layer 209 is substantially uniform.

That is, at a portion of the coating layer 209 where the first protection layer 211 is thick, the second protection layer 213 is thin; by contrast, at a portion of the coating layer 209 where the first protection layer 211 is thin (or does not exist), the second protection layer 213 is thick. Accordingly, the thickness of the coating layer 209 is substantially uniform (at a two-layer structure portion).

Therefore, the second embodiment yields effects similar to those yielded by the first embodiment.

A rear end portion of the coating layer 209 has a single-layer structure composed of the first protection layer 211, and the thickness of the rear end portion is small. However, since the rear end portion of the coating layer 209 is located far away from a region of the detecting section 80 in which the resistance heat-generating element 89 is formed, the temperature of the rear end portion of the coating layer 209 is low. Thus, even in the event of adhesion of water to the rear end portion of the coating layer 209, cracking is not generated.

Third Embodiment

Next, a gas sensor element of a third embodiment will be described. Description of features similar to those of the first embodiment described above is omitted.

The present third embodiment differs from the first embodiment in the structure of the gas sensor element; therefore, the gas sensor element will be mainly described.

Figure 7:
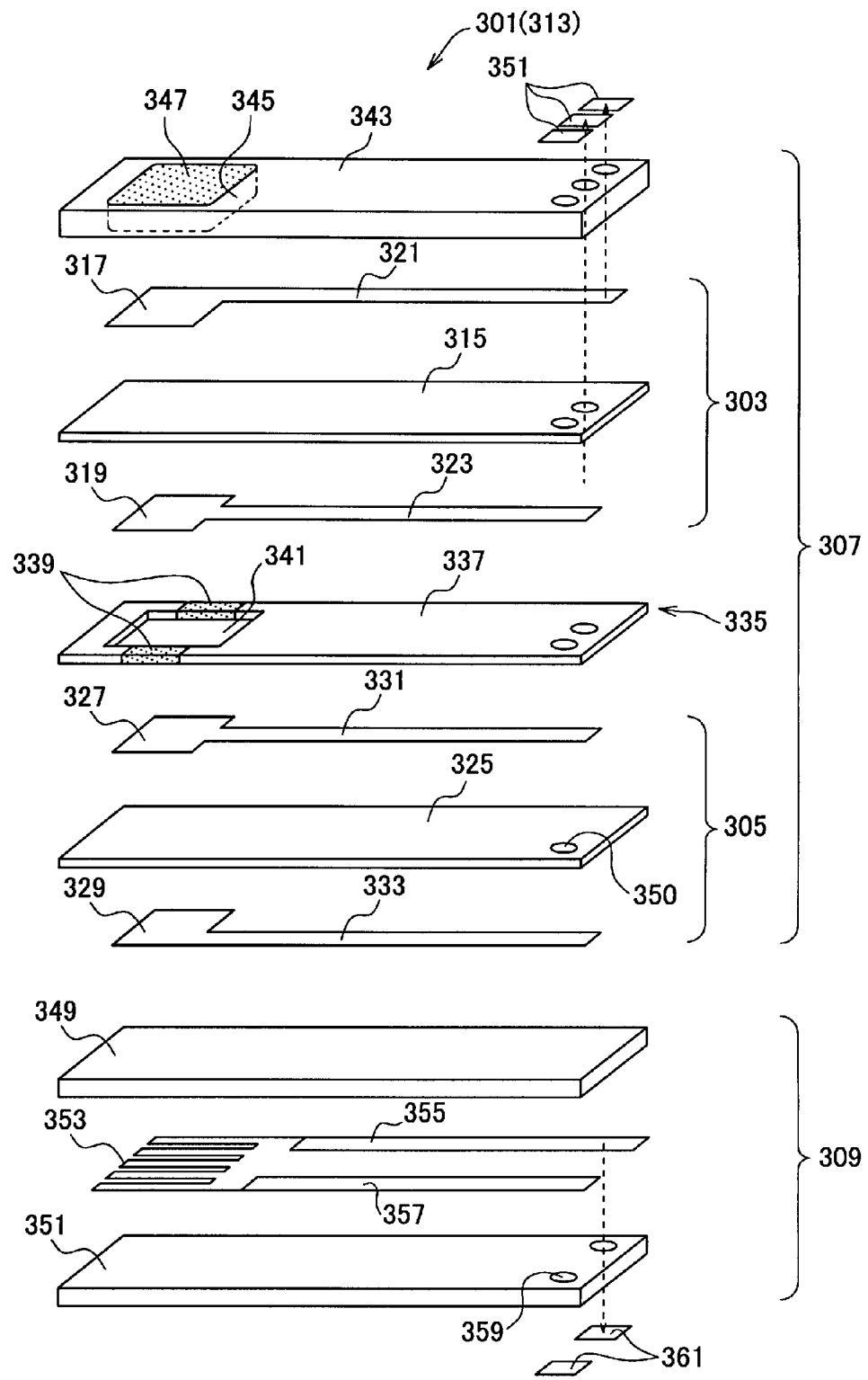
FIG. 7 is an exploded perspective view showing a gas sensor element of a third embodiment of the present invention.

As shown in FIG. 7, a gas sensor element 301 of the third embodiment is an element used in an oxygen sensor for detecting oxygen concentration in, for example, exhaust gas. The gas sensor element 301 includes a detection element 307 having an oxygen pump cell 303 and an oxygen concentration detection cell 305, and a heater element 309 similar to that in the first embodiment.

FIG. 7 shows a gas sensor element body 313 resulting from removal of a coating layer 363 (see FIG. 8) from the gas sensor element 301. The configurational features of the gas sensor element body 313 are briefly described below.

The detection element 307 is a laminate of the oxygen pump cell 303 and the oxygen concentration detection cell 305.

The oxygen pump cell 303 includes a first solid electrolyte layer 315, a first electrode 317 and a second electrode 319 formed on respective opposite surfaces of the first solid electrolyte layer 315, and leads 321 and 323 connected to the first and second electrodes 317 and 319, respectively.

The oxygen concentration detection cell 305 includes a second solid electrolyte layer 325, a third electrode 327 and a fourth electrode 329 formed on respective opposite surfaces of the second solid electrolyte layer 325, and leads 331 and 333 connected to the third and fourth electrodes 327 and 329, respectively.

An insulating layer 335 is formed between the oxygen pump cell 303 and the oxygen concentration detection cell 305. The insulating layer 335 is composed of an insulating portion 337 and a diffusion controlling portion 339.

The insulating layer 335 has a hollow gas detection chamber 341 formed at a position corresponding to the second and third electrodes 319 and 327 (between the two electrodes 319 and 327). The gas detection chamber 341 communicates with an ambient atmosphere along the width direction of the insulating layer 335 through the diffusion controlling portion 339 (which controls diffusion of gas).

Materials used to form the solid electrolyte layers 315 and 325, the electrodes 317, 319, 327, and 329, the leads 321, 323, 331, and 333, etc., are similar to those used in the first embodiment.

The insulating portion 337 is formed of alumina, mullite, or a like electrically insulating material. The diffusion controlling portion 339 is a porous body formed of, for example, alumina.

Also, a dense ceramic layer 343 is formed on the front surface of the first solid electrolyte layer 315 such that the first electrode 317 and the lead 321 are sandwiched therebetween. The ceramic layer 343 has an opening 345 formed at its forward end portion corresponding to the first electrode 317. Similar to the first embodiment, the opening 345 accommodates therein a porous layer 347 which covers the first electrode 317.

Similar to the first embodiment, the heater element 309 is configured such that a resistance heat-generating element 353 and leads 355 and 357 are sandwiched between two ceramic layers 349 and 351.

The leads 321, 323, 331, and 333 of the electrodes 317, 319, 327, and 329 are connected to respective terminals 351 through through holes 350. The leads 355 and 357 of the heater element 309 are connected to respective terminals 361 through through holes 359.

Figure 8:
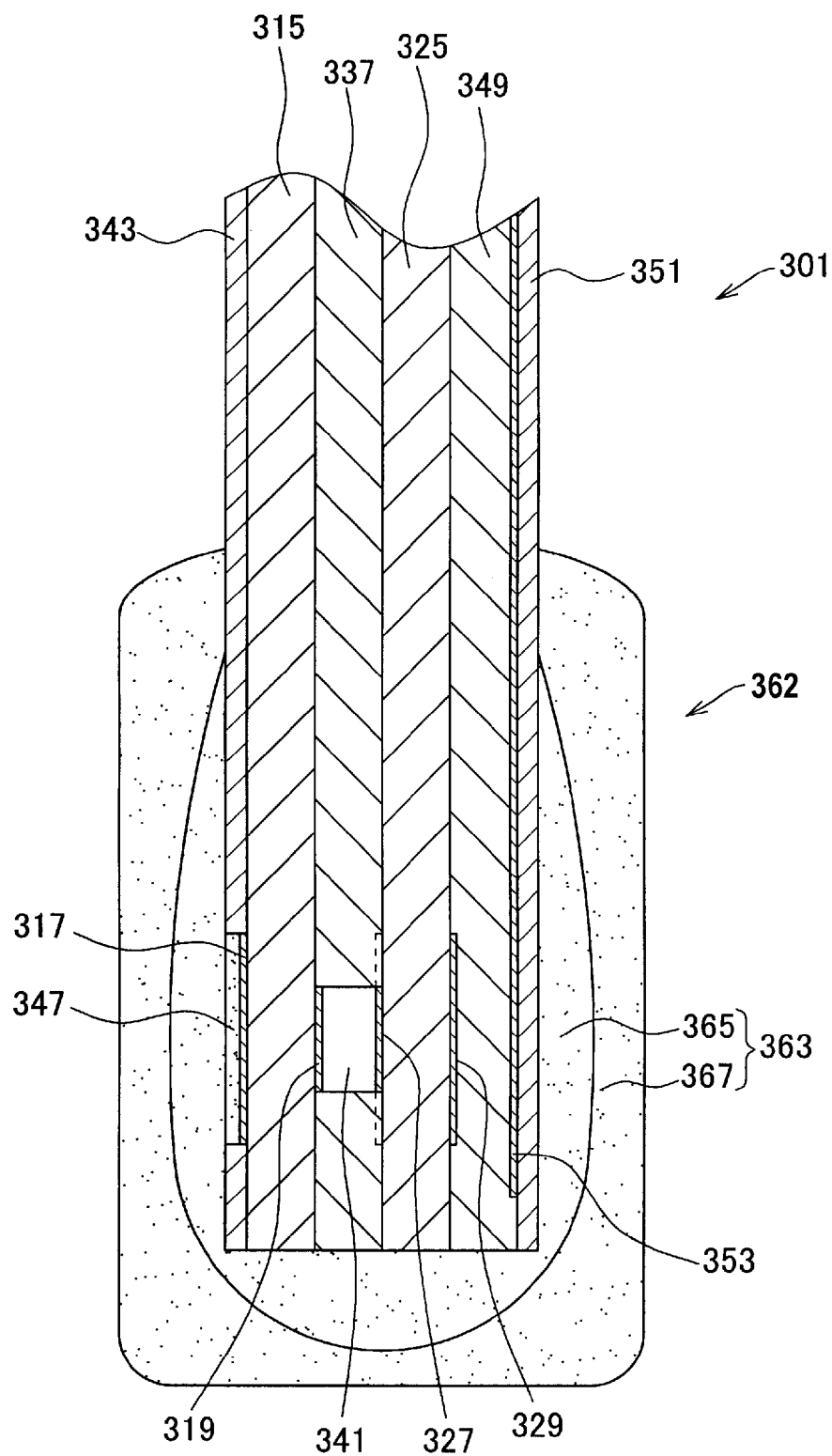
FIG. 8 is a sectional view of a forward end portion of the gas sensor element of the third embodiment taken along the axial direction (a direction perpendicular to the thickness direction).

Furthermore, in the present third embodiment also, as shown in FIG. 8, the gas sensor element 301 has the coating layer 363 formed at its forward end portion 362 in a manner similar to that in the first embodiment.

Specifically, similar to the first embodiment, the coating layer 363 is composed of a lower layer (first protection layer) 365 which covers the forward end portion 362 of the gas sensor element 301, and an upper layer (second protection layer) 367 which covers the first protection layer 365 and extends rearward.

External shapes of the first protection layer 365 and the second protection layer 367 and the thickness relation between the first and second protection layers 365 and 367 are similar to those in the first embodiment.

Specifically, the first protection layer 365 has a substantially spherical shape in such a manner as to swell at its central portion, and the second protection layer 367 is formed in such a manner as to cover the entire first protection layer 365. The coating layer 363 has substantially uniform radial thickness (thickness in a direction perpendicular to the axial direction) along the circumferential direction.

Therefore, the third embodiment yields effects similar to those yielded by the first embodiment.

Experimental Example

Next will be described an experiment conducted to verify effects of the present invention.

In the present experiment, five samples of a gas sensor element similar to that of the first embodiment were manufactured. The samples were measured for the thicknesses of the first protection layer and the second protection layer.

Figure 9A:
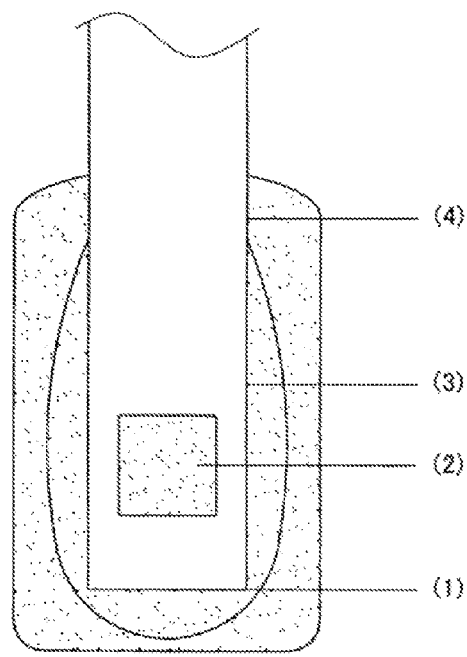
FIG. 9A is an explanatory view showing positions of measuring thicknesses in samples of an example.
Figure 10A:
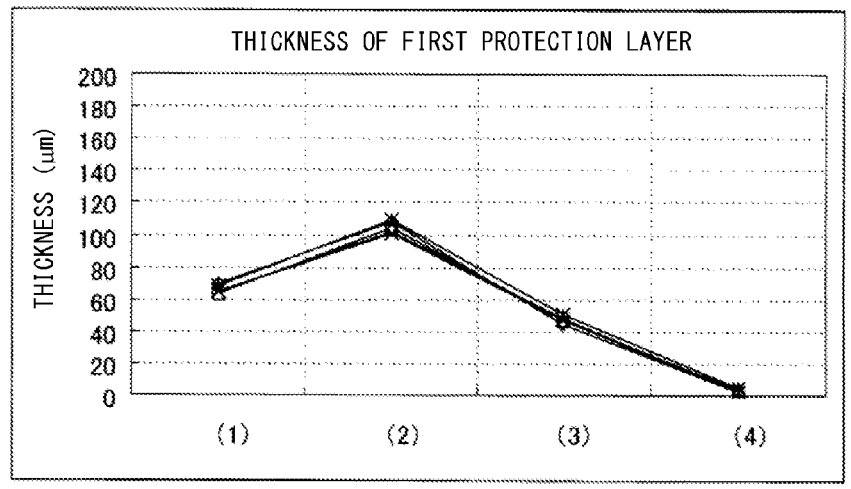
FIGS. 10A to 10C are graphs showing experimental results of the samples of the example.
Figure 10B:
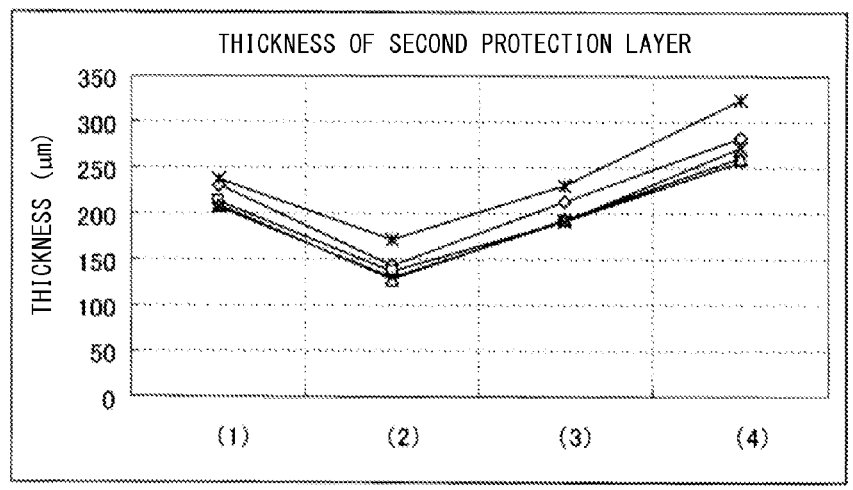
Figure 10C:
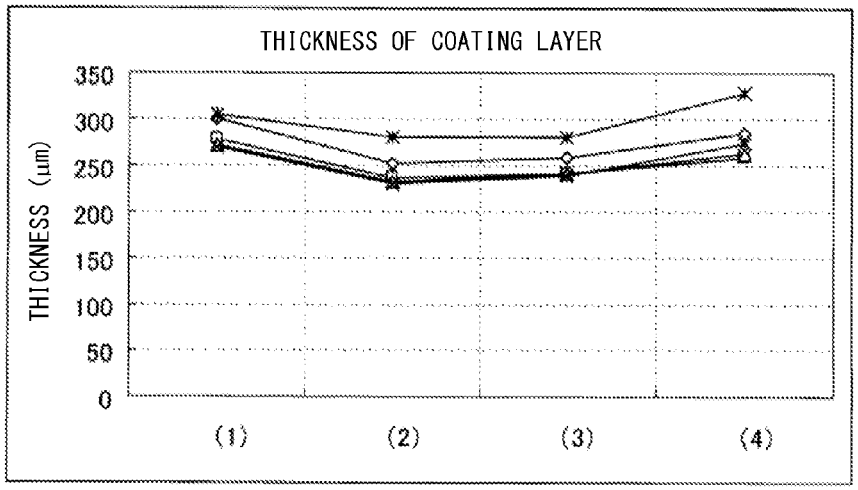

More specifically, as shown in FIG. 9A, measured thicknesses are as follows: thicknesses of the first and second protection layers at the forward end ((1) at the forward end of side surface) of the gas sensor element body; thicknesses of the first and second protection layers at the axial center of the porous layer ((2) on the porous layer); thicknesses of the first and second protection layers at a position located rearward of the porous layer ((3) at a rear end portion); and thicknesses of the first and second protection layers near the rear end of the coating layer ((4) at the rearmost end). FIGS. 10A to 10C show the results of the measurement.

Distances from (1) to (2), (3), and (4) are 3.0 mm, 5.0 mm, and 7.5 mm, respectively. The axial (in FIGS. 9A and 9B, vertical) dimension of the porous layer is 3.0 mm.

FIG. 10A shows data on the thickness of the first protection layer; FIG. 10B shows data on the thickness of the second protection layer; and FIG. 10C shows data on the thickness of the coating layer. In FIGS. 10A to 10C, the vertical axis represents thickness, and the horizontal axis represents the position of measurement.

As is apparent from FIGS. 10A to 10C, the samples of the first embodiment show the following features: the first protection layer is thick at its central portion along the axial direction of the gas sensor element ((2) on the porous layer), whereas the second protection layer is thin at its central portion; thus, the coating layer has substantially uniform thickness as a whole.

In the present experiment, samples of a comparative example were also manufactured; specifically, there were manufactured five samples of a conventional gas sensor element in which the lower layer (first protection layer) and the upper layer (second protection layer) were formed by a dipping process. The thicknesses of the lower and upper layers of each sample were measured.

Figure 9B:
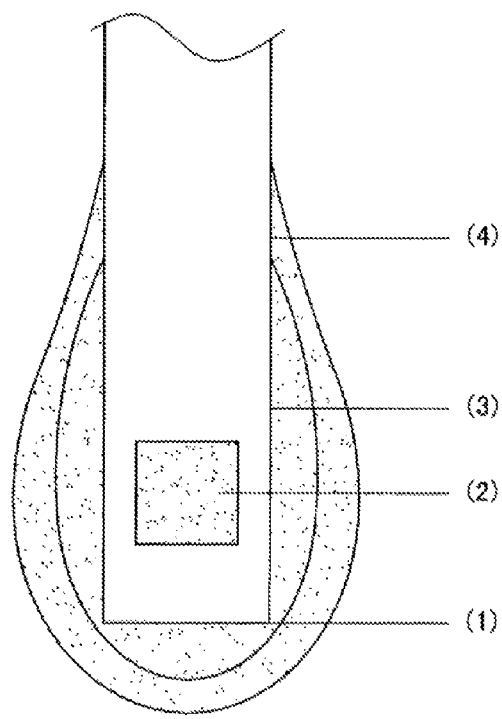
FIG. 9B is an explanatory view showing positions of measuring thicknesses in samples of a comparative example.
Figure 11A:
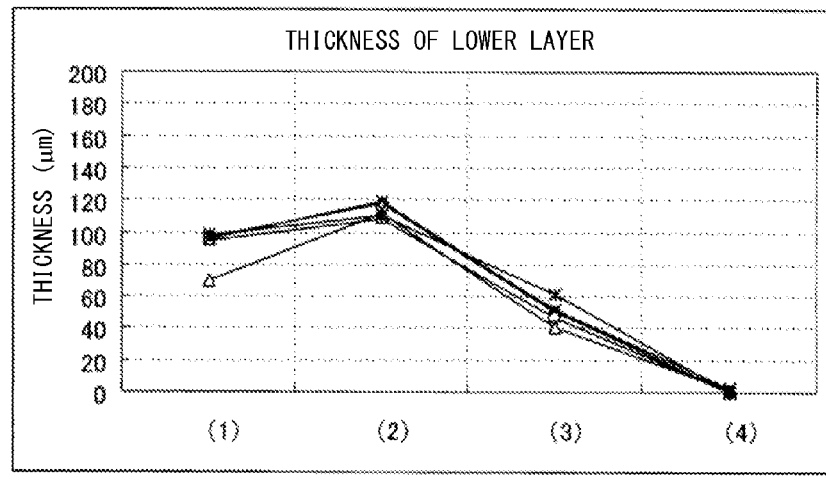
FIGS. 11A to 11C are graphs showing experimental results of the samples of the comparative example.
Figure 11B:
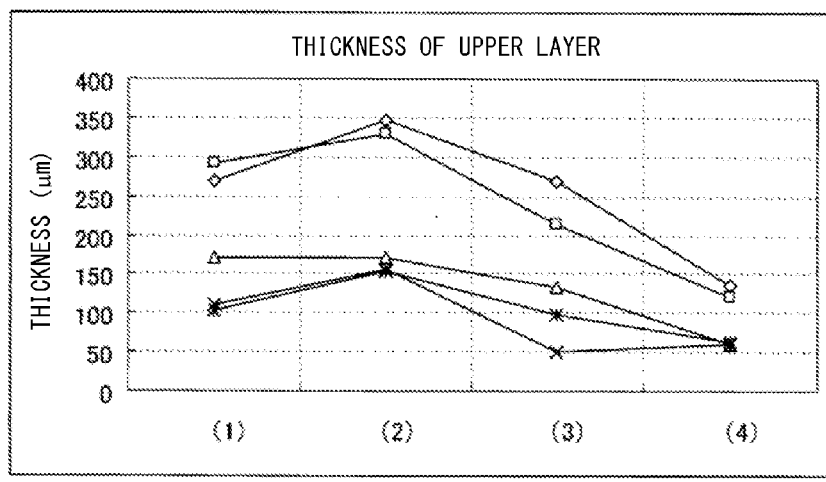
Figure 11C:
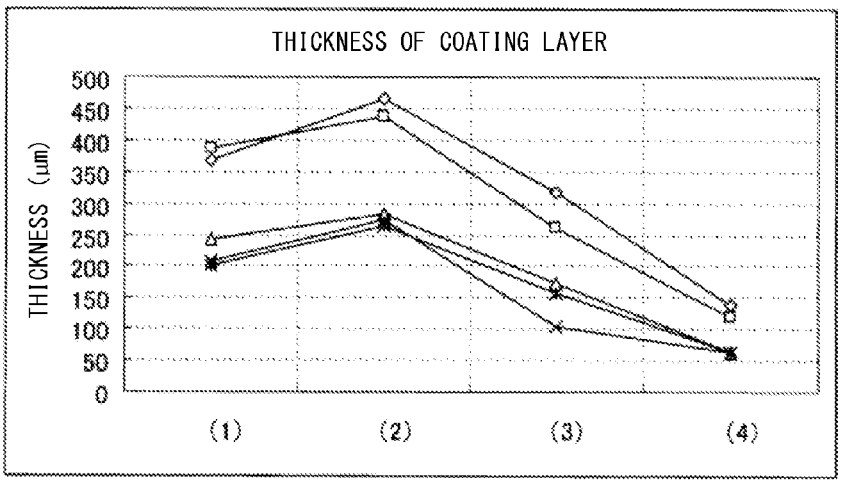
Figure 12:
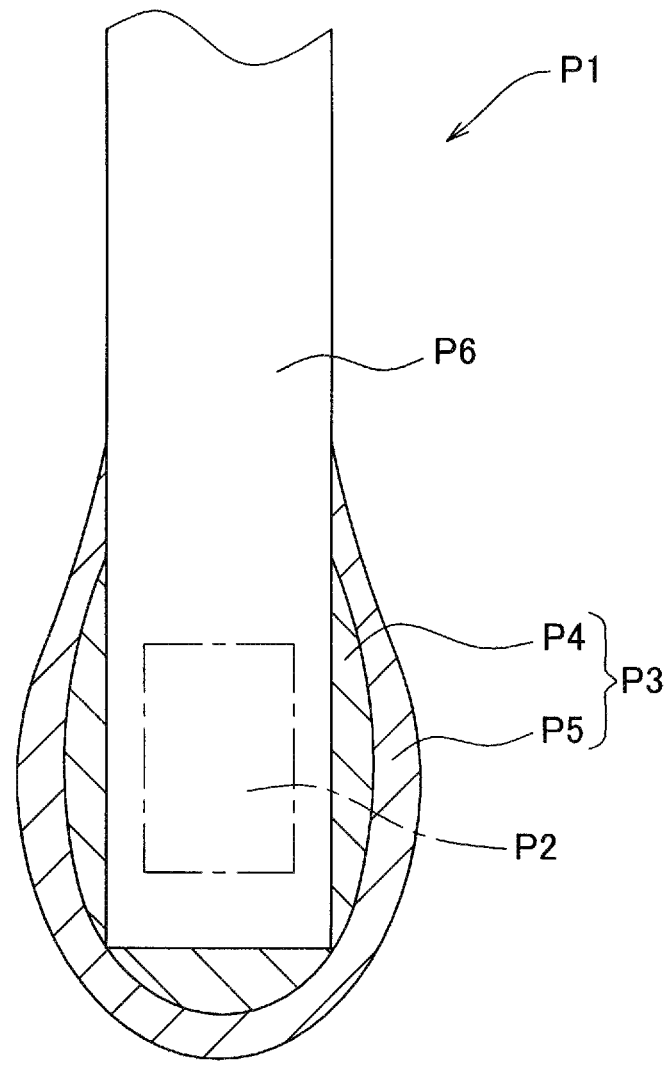
FIG. 12 is an explanatory view for explaining a conventional technique.

More specifically, as shown in FIG. 9B, measured thicknesses are as follows: thicknesses of the lower and upper layers at the forward end ((1) at the forward end of side surface) of the gas sensor element body; thicknesses of the lower and upper layers at the axial center of the porous layer ((2) on the porous layer); thicknesses of the lower and upper layers at a position located rearward of the porous layer ((3) at a rear end portion); and thicknesses of the lower and upper layers at the rear end of the coating layer ((4) at the rearmost end). FIGS. 11A to 11C show the results of the measurement. Positions (1) to (4) of measuring thicknesses and the dimension of the porous layer are similar to those shown in FIG. 9A.

FIG. 11A shows data on the thickness of the lower layer; FIG. 11B shows data on the thickness of the upper layer; and FIG. 11C shows data on the thickness of the coating layer.

In FIGS. 11A to 11C, the vertical axis represents thickness, and the horizontal axis represents the position of measurement.

As is apparent from FIGS. 11A to 11C, the samples of the comparative example show the following features: the lower and upper layers are thick at their central portions along the axial direction of the gas sensor element (thus, the coating layer is thick at its central portion) and are thin at their rear end portions.

The present invention has been described with reference to the embodiments. However, the present invention is not limited thereto, but may be embodied in various other forms.

For example, the first protection layer and the second protection layer may have the same percentage of pores (the same porosity), or the second protection layer may be higher in the percentage of pores than the first protection layer.

In the embodiments of the present invention, the thickness of the coating layer is controlled by combining a dipping process and a spraying process. However, the present invention is not limited thereto. For example, by controlling the amount of application of the outer coating liquid in forming the outer coating layer, the thickness of the coating layer can be controlled as in the case of the present invention.

Also, configurational features of the embodiments may be combined as appropriate.

DESCRIPTION OF REFERENCE NUMERALS

1: gas sensor
7, 201, 301: gas sensor element
8, 203, 313: gas sensor element body
39, 209, 363: coating layer
65, 315, 325: solid electrolyte layer
67, 69, 317, 319, 327, 329: electrode
77, 215, 347: porous layer
80, 207: detecting section
111, 211, 365: first protection layer
113, 213, 327: second protection layer

What is claimed is:

1. A gas sensor element comprising:
an elongated plate-like element including, at a forward end portion, a detecting section comprising a solid electrolyte body having an outer surface and a back surface, a detection electrode on the outer surface and a reference electrode on the back surface of the solid electrolyte body, and a porous layer covering the detection electrode; and
a coating layer including a first protection layer and a second protection layer, the first protection layer entirely covering the detecting section and the second protection layer circumferentially covering the first protection layer and extending at least from a forward end of the first protection layer to a position located rearward of the porous layer,
wherein a thickness of the first protection layer on the porous layer is larger than a thickness of the first protection layer rearward of the porous layer, and
a thickness of the second protection layer in a region where the first protection layer and the second protection layer of the coating layer are superposed on each other along a longitudinal direction of the plate-like element and rearward of the porous layer is larger than a thickness of the second protection layer above the porous layer.

2. The gas sensor element according to claim 1, wherein in a region where the first protection layer and the second protection layer of the coating layer are superposed on each other along a longitudinal direction of the plate-like element, a difference between a largest thickness and a smallest thickness of the coating layer is 100 μm or less.

3. The gas sensor element according to claim 1, wherein the second protection layer entirely covers the first protection layer, and a rear end portion of the coating layer has a single-layer structure comprising the second protection layer.

4. The gas sensor element according to claim 1, wherein the second protection layer covers a forward portion of the first protection layer, and a rear end portion of the coating layer has a single-layer structure comprising the first protection layer.

5. The gas sensor element according to claim 1, wherein the first protection layer is higher in percentage of pores than the second protection layer.

6. The gas sensor element according to claim 1, wherein the second protection layer is thicker than the first protection layer in the entire region of the coating layer.

7. The gas sensor element according to claim 1, further comprising a heater disposed in the plate-like element in a region which is superposed on the detecting section as viewed from a thickness direction of the plate-like element.

8. A gas sensor comprising:
   a gas sensor element according to claim 1, the gas sensor element for detecting a concentration of a particular gas component in gas to be measured; and
   a housing for holding the gas sensor element.

* * * * *